United States Patent
Zou et al.

(10) Patent No.: US 11,981,653 B2
(45) Date of Patent: May 14, 2024

(54) SYNTHESIS METHOD OF CHIRAL (S)-NICOTINE

(71) Applicant: SHENZHEN ZINWI BIO-TECH CO., LTD, Guangdong (CN)

(72) Inventors: Jun Zou, Guangdong (CN); Yang Zou, Guangdong (CN); Meisen Liu, Guangdong (CN); Weixian Luo, Guangdong (CN)

(73) Assignee: SHENZHEN ZINWI BIO-TECH CO., LTD, Shenzhen (CN)

( * ) Notice: Subject to any disclaimer, the term of this patent is extended or adjusted under 35 U.S.C. 154(b) by 262 days.

(21) Appl. No.: 17/718,313

(22) Filed: Apr. 11, 2022

(65) Prior Publication Data

US 2023/0044688 A1 Feb. 9, 2023

(30) Foreign Application Priority Data

Jul. 10, 2021 (CN) .......................... 202110781163.8
Sep. 3, 2021 (CN) .......................... 202111029637.X

(51) Int. Cl.
C07D 401/04 (2006.01)

(52) U.S. Cl.
CPC .................................. *C07D 401/04* (2013.01)

(58) Field of Classification Search
None
See application file for complete search history.

(56) References Cited

FOREIGN PATENT DOCUMENTS

| CN | 104341390 A | 2/2015 |
| CN | 111233829 A | 6/2020 |
| EP | 3925955 A1 | 12/2021 |

OTHER PUBLICATIONS

Loh et al, Tetrahedron Letters, vol. 40, pp. 7847-7850 (Year: 1999).*
European Search Report of European Patent Application No. 21810886.8 dated Nov. 7, 2023.
Kun Huang et al, A New and Efficient Approach to the Synthesis of Nicotine and Anabasine Analogues, Journal of Heterocyclic Chemistry, Nov. 2009, pp. 1252~1258, vol. 46, No. 6.

* cited by examiner

*Primary Examiner* — Zinna Northington Davis

(57) ABSTRACT

The present application discloses a synthesis method of chiral nicotine from nicotinate and γ-butyrolactone, including the following steps: Step S1: performing condensation under an alkaline condition, and performing ring opening reaction with hydrochloric acid; Step S2: reacting with (+)—B-diisopinocampheyl chloroborane to produce a chiral hydroxyl group; Step S3: performing a chlorination reaction; and Step S4: performing cyclization under an alkaline condition to obtain the chiral nicotine. In the present application, nicotinate and γ-butyrolactone, both cheap and readily available, are used as raw materials, so as to reduce the production cost of (S)-nicotine. (+)—B-diisopinocampheyl chloroborane is used to reduce a carbonyl group of an intermediate to obtain a target chiral center. The (+)—B-diisopinocampheyl chloroborane induces the production of a chiral hydroxyl group, chlorination and cyclization are performed to form chiral (S)-demethylnicotine, and finally amine methylation is performed to obtain (S)-nicotine with photochemical activity.

20 Claims, No Drawings

SYNTHESIS METHOD OF CHIRAL (S)-NICOTINE

CROSS-REFERENCE TO RELATED APPLICATION

The present application claims the priority and benefits of Chinese patent application No. 202111029637.X, filed on Sep. 3, 2021, and Chinese patent application No. 202110781163.8, filed on Jul. 10, 2021. The entirety of the above-mentioned patent applications are hereby incorporated by reference herein and made a part of this specification.

TECHNICAL FIELD

The present invention relates to the technical field of chemical synthesis, and particularly relates to a synthesis method of chiral (S)-nicotine.

BACKGROUND ART

With the rapid development of e-cigarette industry, the demand of nicotine, which is one of the important active ingredients of e-cigarette, is increasing, among which nicotine in a single configuration with optical activity is widely concerned. (S)-Nicotine has a molecular formula of $C_{10}H_{14}N_2$, a CAS number of 54-11-5, and a structural formula of

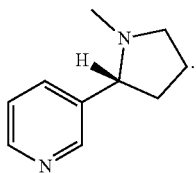

At present, (S)-nicotine is basically obtained by a chiral resolution method, but chiral resolution reagents are expensive, which is not conducive to industrial production of chiral nicotine.

In order to reduce production costs, it is also very important to choose cheap and easily available raw materials. At present, there is no reports on synthesizing (s)-nicotine from cheap and easily available nicotinate and γ-butyrolactone

SUMMARY

In order to reduce the production cost of (S)-nicotine, the application provides a synthesis method of chiral nicotine.

In a first aspect, the present application provides a synthesis method of (S)-nicotine, which is achieved by adopting the following technical solutions:
a synthesis method of (S)-nicotine from nicotinate and γ-butyrolactone as raw materials, including the following steps:
S1: performing condensation under an alkaline condition, and performing ring opening reaction with hydrochloric acid;
S2: reacting with (+)—B-diisopinocampheyl chloroborane to produce a chiral hydroxyl group;
S3: performing a chlorination reaction; and
S4: performing cyclization under an alkaline condition to obtain the chiral nicotine.

In the above technical solution, nicotinate and γ-butyrolactone, both cheap and readily available, are used as raw materials, so as to reduce the production cost of (S)-nicotine. (+)—B-diisopinocampheyl chloroborane is used to reduce a carbonyl group of an intermediate to obtain a target chiral center. The (+)—B-diisopinocampheyl chloroborane induces the production of a chiral hydroxyl group, chlorination and cyclization are performed to form chiral (S)-demethylnicotine, and finally amine methylation is performed to obtain (S)-nicotine with photochemical activity. There is no need of chiral resolution and the production cost of (S)-nicotine can be further reduced.

In the present application, the nicotinate is selected from a group consisting of methyl nicotinate and ethyl nicotinate.

Preferably, an amination reaction is performed between Step S1 and Step S2, and an amine methylation reaction is performed following the cyclization in Step S4.

In a second aspect, the present application provides a synthesis method of chiral nicotine including the following steps:
A1: performing condensation reaction on nicotinate and γ-butyrolactone, and performing ring opening reaction with hydrochloric acid to obtain 4-chloro-1-(3-pyridinyl)-1-butanone;
A2: reacting the 4-chloro-1-(3-pyridinyl)-1-butanone with (+)—B-diisopinocampheyl chloroborane to obtain (S)-4-chloro-1-(pyridin-3-yl)butan-1-ol;
A3: reacting the (S)-4-chloro-1-(pyridin-3-yl)butan-1-ol with a chlorination reagent to obtain (S)-3-(1,4-dichlorobutyl)pyridine; and
A4: performing cyclization reaction on the (S)-3-(1,4-dichlorobutyl) pyridine using an amination under an alkaline condition to obtain S-demethylnicotine or (S)-nicotine; in which the S-demethylnicotine is subjected to amine methylation to obtain (S)-nicotine.

By adopting the above technical solution, the application adopts mild reaction conditions and easy operation and obtains (S)-nicotine of a single configuration by high selectivity. The carbonyl group of 4-chloro-1-(3-pyridine)-1-butanone is reduced by (+)—B-diisopinocampheyl chloroborane to obtain the chiral hydroxyl group. The (S)-4-chloro-1-(pyridin-3-yl)butan-1-ol is firstly subjected to chlorination, and then to a cyclization with an amination reagent under an alkaline condition. This improves the yield of (S)-nicotine. Further, whether there will be an amine methylation can be determined by the kinds of amination reagent. If there is no need of amine methylation, the reaction steps can be significantly reduced, so as to further improve the yield of (S)-nicotine. The (S)-nicotine prepared according to the present application has the advantages of high yield, high purity and high ee value, being suitable for industrial production.

In the present application, in Step A1, an alkaline catalyst is used in the condensation reaction. The alkaline catalyst is one or more selected from the group consisting of alkali metal alkoxide, alkaline earth metal hydride, alkaline earth metal oxide, amine, metal salt of amine, hydroxide, carbonate and bicarbonate.

In the present application, in Step A1, an organic solvent is used in the condensation reaction. The organic solvent I is one or more selected from the group consisting of tetrahydrofuran, methyl tert butyl ether, dimethyl tetrahydrofuran and 1,4-dioxane. Preferably, the organic solvent I is 1,4-dioxane.

In the present application, in Step A1, the reaction is carried out in $N_2$ atmosphere, and the nicotinate, the γ-butyrolactone and the alkaline catalyst is added in the order of firstly γ-butyrolactone, secondly the alkaline catalyst and finally the nicotinate.

In the present application, the γ-butyrolactone and the alkaline catalyst are reacted at 0° C. for 30 min. The nicotinate as added are reacted with the γ-butyrolactone and the alkaline catalyst at 25° C.

In the present application, in Step A1, the molar ratio of a resultant condensation product to HCl in hydrochloric acid is 1: (1-6). Preferably, the molar ratio of the condensation product to HCl in hydrochloric acid is 1:1.

In the present application, in Step A1, a refluxing time of the condensation product and the hydrochloric acid at 70-90° C. is 0.5-1.5h. Preferably, the reflux time of the condensation product and hydrochloric acid at 80° C. is 1h.

In the present application, in Step A2, a reaction temperature of 4-chloro-1-(3-pyridinyl)-1-butanone with (+)—B-diisopinocampheyl chloroborane is -30-10° C. Preferably, the reaction temperature of the 4-chloro-1-(3-pyridinyl)-1-butanone with (+)—B-diisopinocampheyl chloroborane is 0° C.

In the present application, in Step A2, an organic solvent II is used in the reaction of 4-chloro-1-(3-pyridinyl)-1-butanone with (+)—B-diisopinocampheyl chloroborane. The organic solvent II is one or more selected from the group consisting of tetrahydrofuran, dimethyltetrahydrofuran and 1,4-dioxane. Preferably, the organic solvent II is tetrahydrofuran.

In the present application, in Step A2, a molar ratio of 4-chloro-1-(3-pyridinyl)-1-butanone to (+)—B-diisopinocampheyl chloroborane is 1: (1-3). Preferably, the molar ratio of 4-chloro-1-(3-pyridinyl)-1-butanone to (+)—B-diisopinocampheyl chloroborane is 1:2.

In the present application, a reaction temperature of Step A3 is -10-10° C. Preferably, the reaction temperature of Step A3 is 0° C.

In the present application, a reaction time of Step A3 is 20-40 min. Preferably, the reaction time of Step S3 is 30 min.

In the present application, in Step A3, the chlorinated reagent is selected from oxalyl chloride, dichlorosulfoxide, $PCl_3$ and $PCL_5$. More preferably, the chlorination reagent is oxalyl chloride.

In the present application, in Step A3, a molar ratio of (S)-4-chloro-1-(pyridin-3-yl) butan-1-ol to oxalyl chloride is 1: (1-2). Preferably, the molar ratio of (S)-4-chloro-1-(pyridin-3-yl) butan-1-ol to oxalyl chloride is 1:1.5.

Preferably, in Step A4, a reaction temperature under the alkaline condition is 50-80° C.

More preferably, the reaction temperature under the alkaline condition is 60° C.

In the present application, in Step A4, the reaction time under the alkaline condition is 5-6h.

In the present application, in Step A4, a base used under the alkaline condition includes, but not limited to, carbonate, for example, sodium carbonate, potassium carbonate or cesium carbonate. Preferably, the carbonate is potassium carbonate.

In the present application, in Step A4, a molar ratio of (S)-3-(1,4-dichlorobutyl) pyridine to potassium carbonate is 1:(2-4). Preferably, the molar ratio of (S)-3-(1,4-dichlorobutyl) pyridine to potassium carbonate is 1:3.

Preferably, in Step A4, the amination reagent is a methylamine salt amination reagent or an amino amination reagent.

Preferably, when the amination reagent is a methylamine salt amination reagent, (S)-3-(1,4-dichlorobutyl) pyridine reacts with the amination reagent under an alkaline condition to obtain (S)-nicotine.

When the amination reagent is a methylamine salt amination reagent, there is no need of performing subsequent methylation reaction step, and (S)-nicotine can be prepared in four steps, which greatly improves the yield of (S)-nicotine.

Preferably, a molar ratio of (S)-3-(1,4-dichlorobutyl) pyridine to methylamine salt amination reagent is 1: (1-5). More preferably, the molar ratio of (S)-3-(1,4-dichlorobutyl) pyridine to methylamine salt amination reagent is 1:3.

Preferably, the methylamine salt amination reagent is any one selected from the group consisting of methylamine hydrochloride, methylamine sulfate and methylamine nitrate. More preferably, the methylamine salt amination reagent is methylamine hydrochloride.

In this application, in Step A4, after performing cyclization reaction on the (S)-3-(1,4-dichlorobutyl) pyridine using an amination reagent under an alkaline condition, a post-treatment step is further included: adding acid to adjust the pH to 6-7, extracting to obtain an organic phase, spin drying the organic phase to remove solvent, distilling and purifying to obtain (S)-nicotine.

Preferably, when the amination reagent is an amino amination reagent, (S)-3-(1,4-dichlorobutyl) pyridine reacts with the amination reagent under an alkaline condition to obtain (S)-demethylnicotine.

Preferably, a molar ratio of (S)-3-(1,4-dichlorobutyl) pyridine to amino amination reagent is 1: (3-8). More preferably, the molar ratio of (S)-3-(1,4-dichlorobutyl) pyridine to amino amination reagent is 1:4.

Preferably, the amino amination reagent is any one selected from of formamide, tert butyl carbamate and ammonium hydroxide. More preferably, the amino amination reagent is ammonium hydroxide.

In the present application, in Step A4, after performing cyclization reaction on the (S)-3-(1,4-dichlorobutyl) pyridine using an amination reagent under an alkaline condition, a post-treatment step is further included: adding acid to adjust the pH to 6-7, extracting to obtain an organic phase, and spin drying the organic phase to remove solvent to obtain (S)-demethylnicotine.

In the present application, in Step A4, the (S)-demethylnicotine is further subjected to amine methylation reaction using and amine methylation reagent, adjusted to a pH of 6 using an acid, extracted to obtained an organic phase, dried by $Na_2SO_4$, concentrated under reduced pressure to obtain crude S-nicotine, distilled and purified to obtain (S)-nicotine.

In the application, in Step A4, the amine methylation reagent is a mixed solution of formaldehyde and formic acid.

In a third aspect, the present application provides a synthesis method of chiral nicotine adopting the following technical solution:

a synthesis method of chiral nicotine comprising the following steps:

BL: adding nicotinate and γ-butyrolactone to organic solvent I and performing condensation at the present of an alkaline catalyst to obtain a condensation product, and subjecting the condensation product to ring opening at the presence of hydrochloric acid to obtain 4-chloro-1-(3-pyridine)-1-butanone;

B2: reacting 4-chloro-1-(3-pyridine)-1-butanone with an amination reagent under an alkaline condition to obtain 4-amino-1-(3-pyridine)-1-butanone;

B3: reacting 4-amino-1-(3-pyridine)-1-butanone with (+)—B-diisopinocampheyl chloroborane in an organic solvent II at -30-10° C. to obtain (S)-4-amino-1-(pyridin-3-yl) butan-1-ol;

B4: reacting (S)-4-amino-1-(pyridin-3-yl) butan-1-ol with a chlorination reagent to obtain (S)-4-amino-1-(pyridin-3-yl) butyl-1-chloride; and B5: performing cyclization on (S)-4-amino-1-(pyridin-3-yl) butyl-1-chloride at the presence of a base to obtain (S)-demethylnicotine, and reacting (S)-demethylnicotine with an amine methylation reagent to obtain (S)-nicotine.

By adopting the above technical solution, nicotinate and γ-butyrolactone are condensed and then ring opened to provide 4-chloro-1-(3-pyridine)-1-butanone, which is first reacted with an amination reagent, then induced to produce a chiral hydroxyl group by using (+)—B-diisopinocampheyl chloroborane, then chlorinated and cyclized to obtain chiral (S)-demethylnicotine, and finally subjected to amine methylation to obtain photochemically active (S)-nicotine. The synthesis method of chiral nicotine provided by the present application has the advantages of high purity, simple steps, easy operation, high yield and mild reaction conditions. It can obtain an S-nicotine with single configuration with high ee value, and thus is suitable for industrial production.

Preferably, in Step B1, a mole ratio of nicotinate, γ-butyrolactone and the alkaline catalyst is 1: (1-2): (1.2-3). More preferably, the molar ratio of nicotinate, γ-butyrolactone and the alkaline catalyst is 1:1:2.

Preferably, in Step B1, the alkaline catalyst is one or more selected from the group consisting of alkali metal alkoxide, alkaline earth metal hydride, alkaline earth metal oxide, amine, metal salt of amine, hydroxide, carbonate and bicarbonate.

In the present application, the alkali metal alkoxide includes, but not limited to, any one selected from the group consisting of sodium tert-butoxide, sodium methoxide, sodium ethoxide and potassium tert-butoxide.

In the present application, the alkaline earth metal hydride includes, but not limited to, one or more selected from the group consisting of NaH, LiH and KH.

In the present application, the alkaline earth metal oxide includes, but not limited to, one or more selected from the group consisting of $Na_2O$, $Li_2O$ and $K_2O$.

In the present application, the amine includes, but not limited to, triethylamine and/or lithium diisopropylamide.

In the present application, the metal salt of amine includes, but not limited to, sodium di(trimethylsilyl) amide and/or lithium diisopropyl amide.

In the present application, the hydroxide includes, but not limited to, one or more selected from the group consisting of sodium hydroxide, lithium hydroxide and magnesium hydroxide.

In the present application, the carbonate includes, but not limited to, one or more selected from the group consisting of sodium carbonate, potassium carbonate and cesium carbonate.

In the present application, the bicarbonate includes, but not limited to sodium bicarbonate and/or potassium bicarbonate.

More preferably, the alkaline catalyst is any one selected from the group consisting of sodium tert-butoxide, NaH and potassium tert-butoxide.

In the present application, in Step B1, the organic solvent I is one or more selected from the group consisting of tetrahydrofuran, methyl tert-butyl ether, dimethyl tetrahydrofuran and 1,4-dioxane. Preferably, the organic solvent I is 1,4-dioxane.

In the present application, in Step B1, the condensation product is subjected to ring opening at the presence of hydrochloric acid, and then is subjected to post-treatment to obtain the 4-chloro-1-(3-pyridine)-1-butanone. The post-treatment includes: diluting with brine, neutralizing with alkaline substance, extracting to obtain an organic phase, and drying to remove a solvent to obtain the 4-chloro-1-(3-pyridine)-1-butanone.

In the present application, before the reaction in Step B2, the 4-chloro-1-(3-pyridine)-1-butanone obtained in Step S1 is dissolved in a solvent. The solvent includes, but not limited to, one or more selected from the group consisting of acetonitrile, 1,4-dioxane, dichloromethane, DMF and tetrahydrofuran. Preferably, the solvent is acetonitrile.

In the present application, in Step B2, a reaction temperature of the 4-chloro-1-(3-pyridine)-1-butanone with the amination reagent under the alkaline condition is 60-100° C., and a reaction time is 6-10h. Preferably, the reaction temperature of the 4-chloro-1-(3-pyridine)-1-butanone with the amination reagent under the alkaline condition is 80° C. and the reaction time is 8h.

Preferably, in Step B2, a molar ratio of the 4-chloro-1-(3-pyridine)-1-butanone to the amination reagent is 1:(1-3). More preferably, the molar ratio of the 4-chloro-1-(3-pyridine)-1-butanone to the amination reagent is 1:2.

Preferably, in Step B2, the amination reagent is ammonia or formamide. More preferably, the amination reagent is formamide.

In the present application, in Step B2, a pH under the alkaline condition for the 4-chloro-1-(3-pyridine)-1-butanone to react with the amination reagent is 8-12. Preferably, the pH under the alkaline condition for the 4-chloro-1-(3-pyridine)-1-butanone to react with the amination reagent is 9. The alkaline condition can be obtained by adjusting with 52 wt % NaOH aqueous solution.

In the present application, Step B2 further includes a post-treatment step, including: adding acid to adjust the pH to 6-7, extracting to obtain an organic phase, and spin drying to remove a solvent in the organic phase to obtain 4-amino-1-(3-pyridine)-1-butanone.

In the present application, in Step B3,4-amino-1-(3-pyridine)-1-butanone prepared in Step S2 is dissolved in the organic solvent II.

Preferably, in Step B3, the organic solvent II is one or more selected from the group consisting of tetrahydrofuran, dimethyltetrahydrofuran and 1,4-dioxane. More preferably, the organic solvent II is tetrahydrofuran.

Preferably, in Step B3, a molar ratio of the 4-amino-1-(3-pyridine)-1-butanone to (+)—B-diisopinocampheyl chloroborane is 1:(1-3). More preferably, the molar ratio of the 4-amino-1-(3-pyridine)-1-butanone to (+)—B-diisopinocampheyl chloroborane is 1: (1.5-2).

Preferably, in Step B3, a reaction temperature of 4-amino-1-(3-pyridine)-1-butanone with (+)—B-diisopinocampheyl chloroborane is 0 and a reaction time is 2h.

In the present application, Step B3 further includes extracting with dichloromethane as an extractant, and then spin drying to remove a solvent to obtain (S)-4-amino-1-(pyridin-3-yl) butan-1-ol.

In the present application, in Step B4, the (S)-4-amino-1-(pyridin-3-yl) butan-1-ol prepared in Step B3 is dissolved in a solvent before reacting with the chlorinated reagent. The solvent includes, but not limited to, 1,4-dioxane.

Preferably, a reaction temperature of Step B4 is -10-10° C. More preferably, the reaction temperature of Step B4 step is 0° C.

In the present application, a reaction time of Step B4 step is 20-40 min. Preferably, the reaction time of Step B4 step is 30 min.

Preferably, in Step B4, the chlorination reagent is selected from oxalyl chloride, dichlorosulfoxide, $PCl_3$ and $PCL_5$. More preferably, the chlorination reagent is oxalyl chloride.

Preferably, in Step B4, a molar ratio of (S)-4-amino-1-(pyridin-3-yl) butan-1-ol to oxalyl chloride is 1:(1-2). More preferably, the molar ratio of (S)-4-amino-1-(pyridin-3-yl) butan-1-ol to oxalyl chloride is 1:1.5.

In the present application, in Step B4, after reacting (S)-4-amino-1-(pyridin-3-yl) butan-1-ol with a chlorination reagent, quenching is performed to obtain a mixture containing (S)-4-amino-1-(pyridin-3-yl) butyl-1-chloride. Water can be selected as a quenching reagent.

In the present application, in Step B5, the mixture containing (S)-4-amino-1-(pyridin-3-yl)butyl-1-chloride prepared in Step B4 is cyclized at the presence of the base to form (S)-demethylnicotine.

Preferably, in Step B5, the base is hydroxide or carbonate.

In the present application, the hydroxide includes, but not limited to, one or more selected from the group consisting of sodium hydroxide, potassium hydroxide, lithium hydroxide, cesium hydroxide, barium hydroxide and magnesium hydroxide.

In the present application, the carbonate includes, but not limited to, one or more selected from the group consisting of sodium carbonate, potassium carbonate and cesium carbonate.

More preferably, the base is sodium hydroxide.

In the application, in Step B5, a molar ratio of (S)-4-amino-1-(pyridin-3-yl) butyl-1-chloride to sodium hydroxide is 1:(1.5-2.5). Preferably, the molar ratio of (S)-4-amino-1-(pyridin-3-yl) butyl-1-chloride to sodium hydroxide is 1:2.

In the present application, in Step B5, a reaction temperature of the mixture containing (S)-4-amino-1-(pyridin-3-yl) butyl-1-chloride prepared in Step B4 with the base is 55-65° C., and a reaction time is 2-3h. Preferably, the reaction temperature of the mixture containing (S)-4-amino-1-(pyridin-3-yl)butyl-1-chloride prepared in Step B4 with the base is 60° C. and the reaction time is 2h.

In the present application, in Step B5, the amine methylation reagent is methyl iodide.

In the present application, in Step B5, a molar ratio of (S)-demethylnicotine to iodomethane is 1:(1.1-1.4). Preferably, the molar ratio of (S)-demethylnicotine to methyl iodide is 1:1.2.

In the present application, in Step B5, a reaction temperature of (S)-demethylnicotine with the amine methylation reagent is 20-30° C., and a reaction time is 2-4h. Preferably, the reaction temperature of (S)-demethylnicotine with the amine methylation reagent is 25° C., and the reaction time is 3h.

In the present application, in Step B5, after the reaction of (S)-demethylnicotine with the amine methylation reagent, the pH is adjusted to 6 with an acid, and extracted to obtain an organi phase. The organic phase is dried by $Na_2SO_4$, concentrated under reduced pressure to obtain crude (S)-nicotine, and the crude (S)-nicotine is purified by atmospheric distillation for one time to obtain (S)-nicotine.

In a fourth aspect, the present application provides a synthesis method of chiral nicotine from butyrolactone, comprising the following steps:

Step C1: performing condensation reaction on nicotinate and γ-butyrolactone, and performing ring opening reaction with hydrochloric acid to obtain 4-chloro-1-(3-pyridinyl)-1-butanone;

Step C2: reacting the 4-chloro-1-(3-pyridinyl)-1-butanone with (+)—B-diisopinocampheyl chloroborane to obtain (S)-4-chloro-1-(pyridin-3-yl)butan-1-ol;

Step C3: reacting the (S)-4-chloro-1-(pyridin-3-yl)butan-1-ol with a chlorination reagent to obtain (S)-3-(1,4-dichlorobutyl) pyridine; and Step C4: performing cyclization reaction on the (S)-3-(1, 4-dichlorobutyl) pyridine using an amination reagent under an alkaline condition to obtain S-demethylnicotine or (S)-nicotine, in which the S-demethylnicotine is subjected to amine methylation to obtain (S)-nicotine.

In summary, the present application has the following beneficial effects.

The application adopts cheap and easily available nicotinate and γ-butyrolactone as starting materials, and eliminates the need for chiral resolution. The cost of single optically active (S)-nicotine is low. The present application involves in simple reaction route, mild reaction conditions, and easy operation, and can obtain (S)-nicotine with single configuration, high yield and purity, at high selectivity. The present application involves in simple steps, and is especially suitable for the production of industrialized (S)-nicotine.

DETAILED DESCRIPTION

The present application will be described in detail below in conjunction with Examples.

Examples

When the amination reagent is methylamine salt amination reagent, the method for synthesizing chiral nicotine from butyrolactone provided in the application is shown in reaction formula 1:

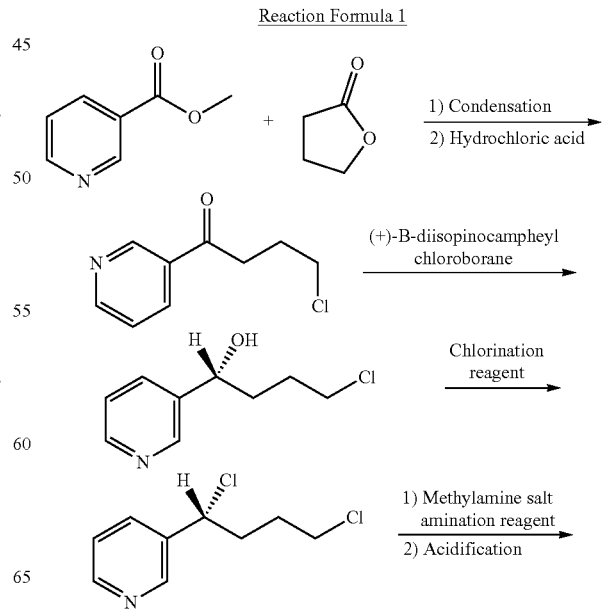

-continued

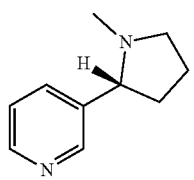

A method for synthesizing chiral nicotine from butyrolactone is provided in Example 1, in which the amination reagent is methylamine salt amination reagent (specifically methylamine hydrochloride), the synthesis route is shown in reaction formula 1, and the specific preparation steps of (S)-nicotine includes:

A1: adding 86.1g (1mol, 1eq) γ-butyrolactone to 1L DMF, stirring at 0° C. for 10 min, adding 48g (2 mol, 2eq) NaH to react at 0° C. for 0.5h, and then adding 137.1g (1 mol) methyl nicotinate to allow for condensation at 25° C. for 2h, and TCL monitoring the reaction until the end of the reaction to obtain a condensation product; and adding 0.831 12mol/L (1mol, 1eq) hydrochloric acid to the condensation product, refluxing at 80° C. for 1h, then extracting with saturated brine, adding sodium bicarbonate to adjust pH of the system to pH 7, extracting with dichloromethane for 3 times, combining organic phases, and spin drying to remove solvent to obtain 4-chloro-1-(3-pyridine) -1-butanone;

A2: dissolving 4-chloro-1-(3-pyridine)-1-butanone obtained in Step A1 with 5L tetrahydrofuran, adding 641.5g (2 mol, 2eq) (+)—B-diisopino- campheyl chloroborane at 0° C. to react at 0 for 2h, extracting with dichloromethane for three times, spin drying to remove solvent to obtain (S)-4-chloro-1- (pyridin-3-yl) butan-1-ol;

A3: adding 2L 1,4-dioxane to (S)-4-chloro-1- (pyridin-3-yl) butan-1-ol obtained in step A2, mixing, adding 190.4g (1.5 mol, 1.5eq) sulfoxide chloride at 0° C., react at 40° C. for 1b, and adding 10 ml water to quench the reaction to obtain a mixture containing (S)-3-(1,4-dichlorobutyl) pyridine; and A4: adding 400g potassium carbonate (3 mol, 3eq) and 201g (3 mol, 3eq) methylamine hydrochloride to the mixture containing (S)-3l,4-dichlorobutyl) pyridine obtained in Step A3, reacting under sealing condition at 60° C. for 6h, adjusting the pH to 6 with 4 mol/L hydrochloric acid after the reaction, extracting with ethyl acetate to obtain an organic phase, spin evaporating to remove the solvent to obtain crude (S)-nicotine; and purifying crude (S)-nicotine by one atmospheric distillation to obtain (S)-nicotine, with a yield of 75%, ee value of 98%, and a purity of 98%.

Examples 2-3 differ from example 1 only in that, in Step A4, different methylamine salt amination reagents were selected, as shown in Table 1.

TABLE 1

Effect of selected methylamine salt amination reagents on the yield of (S)-nicotine

| No. | methylamine salt amination reagents | yield of (S)-nicotine (%) |
| --- | --- | --- |
| Example 1 | methylamine hydrochloride | 75 |
| Example 2 | methylamine sulfate | 72 |
| Example 3 | methylamine nitrate | 70 |

Examples 4-7 differ from example 1 only in that the use amount of methylamine hydrochloride is varied in Step A4 reaction, as shown in Table 2.

TABLE 2

Effect of the use amount of methylamine hydrochloride on the yield of (S)-nicotine

| No. | Eq. of methylamine hydrochloride (eq) | yield of (S)-nicotine (%) |
| --- | --- | --- |
| Example 1 | 3 | 75 |
| Example 4 | 1 | 52 |
| Example 5 | 2 | 68 |
| Example 6 | 4 | 71 |
| Example 7 | 5 | 70 |

When the amination reagent is an amino amination reagent, the synthetic route of the method for synthesizing chiral nicotine from butyrolactone provided in the application is shown in reaction formula 2:

Reaction Formula 2

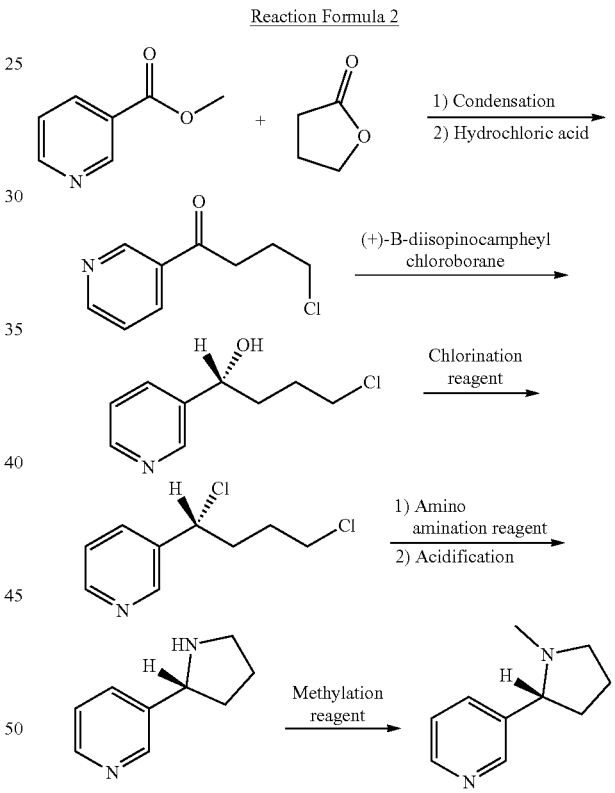

A method for synthesizing chiral nicotine from butyrolactone was provided in Example 8, in which the amination reagent is an amino amination reagent (specifically ammonium hydroxide), the synthesis route is shown in reaction formula 2, and the specific preparation steps of (S)-nicotine includes:

A1. adding 86.1g (1mol, 1eq) γ-butyrolactone to 1L DMF at 0° C., stirring at 0° C. for 10 min, adding 48g (2 mol, 2eq) NaH to react at 0° C. for 0.5h, and then adding 137.1g (1mol) methyl nicotinate to allow for condensation at 25° C. for 2h, and TCL monitoring the reaction until the end of the reaction to obtain a condensation product; and adding 0.831 12 mol/L (1mol, 1eq) hydrochloric acid to the condensation product, refluxing at 80° C. for 1h, then extracting with saturated brine, adding sodium bicarbonate to adjust pH of the system to pH 7, extracting with dichloromethane for 3 times, combining organic phases, and spin drying to remove solvent in the organic phase to obtain 4-chloro-1-(3-pyridine) - 1-butanone;

A2: dissolving 4-chloro-1-(3-pyridine)-1-butanone obtained in Step A1 with 5L tetrahydrofuran, adding 641.5g (2 mol, 2eq) (+)—B-diisopinocampheyl chloroborane at 0° C. to react at 0° C. for 2h, extracting with dichloromethane for three times, spin drying to remove solvent to obtain (S)-4-chloro-1-(pyridin-3-yl) butan-1-ol;

A3: adding 2L 1,4-dioxane to (S)-4-chloro-1-(pyridin-3-yl) butan-1-ol obtained in step A2, mixing, adding 190.4g (1.5 mol, 1.5eq) sulfoxide chloride at 0° C., reacting at 40° C. for 1h, and adding 10 ml water to quench the reaction to obtain a mixture containing (S)-3-(1,4-dichlorobutyl) pyridine;

A4: adding 400g potassium carbonate (3 mol, 3eq) and 140.2g (4 mol, 4eq) ammonium hydroxide to the mixture containing (S)-3-(1,4-dichlorobutyl) pyridine, reacting at 60° C. for 5h, adjusting the pH to 6 with 4 mol/L hydrochloric acid after the reaction, extracting with ethyl acetate to obtain an organic phase, and spin evaporating to remove the solvent to obtain (S)-demethylnicotine; and A5: adding 168g 37 wt % formaldehyde solution and 541g 88WT % formic acid solution to the (S)-demethylnicotine obtained in Step A4, reacting at 60° C. for 3h, adjusting the pH to 6, extracting with a mixed solution of dichloromethane and methanol (the volume ratio of dichloromethane to methanol is 10:1) for three times, combining organic phases, drying the organic phase with Na₂SO₄, concentrating under reduced pressure to remove solvent to obtain crude (S)-nicotine; and purifying (S)-nicotine by one atmospheric distillation to obtain (S)-nicotine, with a yield of 72%, ee value of 98% and purity of 98%.

Examples 9-10 differ from example 8 only in that different amino amination reagent were selected in Step A4 reaction, as shown in Table 3.

TABLE 3

Effect of selected amino amination reagents on the yield of (S)-nicotine

| No. | selected amino amination reagents | yield of (S)-nicotine (%) |
| --- | --- | --- |
| Example 8 | ammonium hydroxide | 72 |
| Example 9 | formamide | 63 |
| Example 10 | tert-butyl carbamate | 65 |

Examples 11-15 differ from example 8 only in that the use amount of ammonium hydroxide is varied in Step A4 reaction, as shown in Table 4.

TABLE 4

Effect of the use amount of ammonium hydroxide on the yield of (S)-nicotine

| No. | eq. of methylamine hydrochloride (eq) ammonium hydroxide (eq) | yield of (S)-nicotine (%) |
| --- | --- | --- |
| Example 8 | 4 | 72 |
| Example 11 | 3 | 60 |

TABLE 4-continued

Effect of the use amount of ammonium hydroxide on the yield of (S)-nicotine

| No. | eq. of methylamine hydrochloride (eq) ammonium hydroxide (eq) | yield of (S)-nicotine (%) |
| --- | --- | --- |
| Example 12 | 5 | 71 |
| Example 13 | 6 | 70 |
| Example 14 | 7 | 68 |
| Example 15 | 8 | 67 |

Example 16 provides a preparation method of (S)-nicotine, in which nicotinate is methyl nicotinate and a synthetic route is shown as Reaction Formula 3:

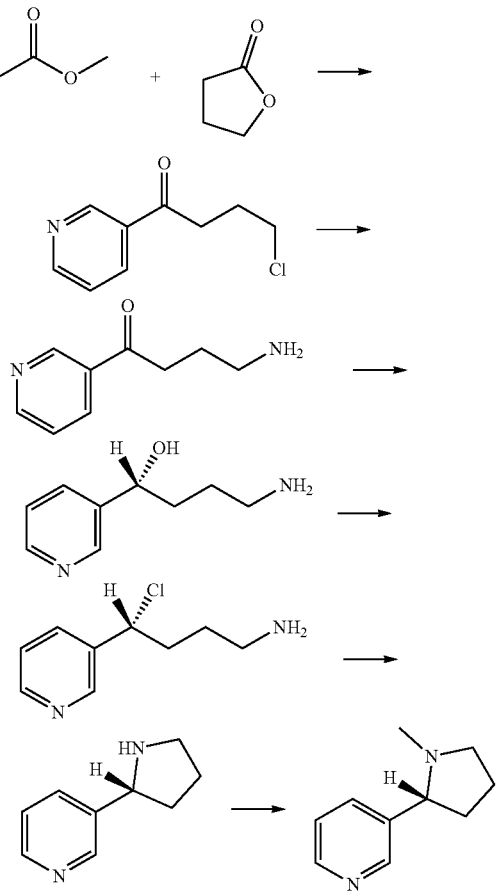

Reaction Formula 3

Specific preparation steps were as follows:

Step B1: addinng 86.1 g (1 mol, 1 eq) of γ-butyrolactone (with a CAS No. of 96-48-0) into I L of 1,4-dioxane at 0° C. mixing, adding 48 g (2 mol, 2 eq) of sodium hydride, reacting at 0'C for 0.5 h, adding 137.1 g (1 mol) of methyl nicotinate (with a CAS No. of 93-60-7), performing a condensation reaction at 25° C. TLC monitoring the reaction until the end of the reaction to obtain a condensation product, adding 0.083 L of 12 mol/L (1 mol, I eq) hydrochloric acid into the condensation product, refluxing at 80'C for 1 h, extracting with saturated salt solution, adding sodium bicarbonate to adjust the pH of the system to pH 7, extracting with dichloromethane for three times, combining organic phases, and spin drying to remove solvent to obtain 4-chloro-1-(pyridin-3-yl)-1-butanone;

Step B2: dissolving the 4-chloro-1-(pyridin-3-yl)-1-butanone obtained in Step B1 in 1 L of acetonitrile, adding 52 wt % NaOH aqueous solution to adjust pH of the system to pH 9, adding 90.1 g (2 mol, 2 eq) of formamide, reacting at 80° C. for 8 h, adding 4 mol/L hydrochloric acid to adjust the pH to 6, extracting with ethyl acetate to obtain an organic phase, and spin evaporating to remove the solvent to obtain 4-amino-1-(pyridin-3-yl)-1-butanone;

Step B3: dissolving the 4-amino-1-(pyridin-3-yl)-1-butanone obtained in Step B2 in 5 L of tetrahydrofuran, adding 641.5 g (2 mol, 2 eq) of (+)—B-diisopinocampheyl chloroborane at 0° C. to react at 0° C. for 2 h, extracting with dichloromethane for three times, and spin drying to remove the solvent to obtain (S)-4-amino-1-(pyridin-3-yl)butan-1-ol;

Step B4: adding 2 L of 1,4-dioxane into the (S)-4-amino-1-(pyridin-3-yl)butan-1-ol obtained in Step B3, mixing, adding 190.4 g (1.5 mol, 1.5 eq) of oxalyl chloride at 0° C., reacting at 0° C. for 30 min, and quenching the reaction by adding 10 mL of water to obtain a mixture containing (S)-4-amino-1-(pyridin-3-yl)butyl-1-chloride; and Step B5: adding 80 g (2 mol, 2 eq) of NaOH into the mixture containing (S)-4-amino-1-(pyridin-3-yl)butyl-1-chloride prepared in Step B4, stirring at 60° C. to react for 2h to obtain a mixture containing (S)-demethylnicotine, adding 170.3 g (1.2 mol, 1.2 eq) of methyl iodide into the mixture containing (S)-demethylnicotine, reacting at 25° C. for 3 h, adjusting the pH of the system to 6 with 12 mol/L hydrochloric acid, extracting with dichloromethane to obtain an organic phase, drying over $Na_2SO_4$, concentrating under reduced pressure to remove solvent to obtain crude (S)-nicotine, and further purifying the crude (S)-nicotine for one time by atmospheric distillation to obtain (S)-nicotine with a yield of 52%, an ee value of 98%, and a purity o 99%.

Examples 17-18 differ from example 16 only in that the type of basic catalyst is varied in the Step B1 reaction, as shown in Table 5.

TABLE 5

Effect of selected base catalyst on the yield of (S)-nicotine

| No. | selected base catalyst | yield of (S)-nicotine (%) |
|---|---|---|
| Example 16 | sodium hydride | 52 |
| Example 17 | sodium tert-butoxide | 42 |
| Example 18 | potassium tert-butoxide | 43 |

Example 19 is different from example 16 only in that the type of amination reagent is varied in Step B2 reaction, as shown in Table 6.

TABLE 6

Effect of selected amination reagents on the yield of (S)-nicotine

| No. | selected amination reagent | yield of (S)-nicotine (%) |
|---|---|---|
| Example 16 | formamide | 52 |
| Example 19 | ammonium hydroxide | 48 |

Examples 20-21 differ from example 16 only in that in Step B2 reaction, the use amount of amination reagents is varied, as shown in Table 7.

TABLE 7

Effect of the use amount of amination reagents on the yield of (S)-nicotine

| Serial number | eq. of amination reagents (eq) | yield of (S)-nicotine (%) |
|---|---|---|
| Example 16 | 2 | 52 |
| Example 20 | 3 | 48 |
| Example 21 | 1 | 45 |

Examples 22-24 differ from example 16 only in that the use amount of (+)—B-diisopinocampheyl chloroborane is varied in Step B3 reaction, as shown in Table 8.

TABLE 8

Effect of the use amount of (+)-B-diisopinocampheyl chloroborane on the yield of (S)-nicotine

| No. | eq. (eq) of (+)-B-diisopinocampheyl chloroborane | yield of (S)-nicotine (%) |
|---|---|---|
| Example 16 | 2 | 52 |
| Example 22 | 1 | 42 |
| Example 23 | 3 | 46 |
| Example 24 | 1.5 | 48 |

Examples 25-27 differ from example 16 only in that the type of organic solvent II is varied in Step B3 reaction, as shown in Table 9.

TABLE 9

Effect of selected organic solvent II on the yield of (S)-nicotine

| No. | selected organic solvents II | yield of (S)-nicotine (%) |
|---|---|---|
| Example 16 | tetrahydrofuran | 52 |
| Example 25 | 1,4-dioxane | 50 |
| Example 26 | methyl tert-butyl ether | 25 |
| Example 27 | absolute ether | 48 |

Examples 28-30 differ from example 16 only in that the reaction temperature is varied in Step B3 reaction, as shown in table 10.

TABLE 10 effect of reaction temperature on the yield of (S)-nicotine

| No. | reaction temperature (° C.) | yield of (S)-nicotine (%) |
|---|---|---|
| Example 16 | 0 | 52 |
| Example 28 | −30 | 50 |

TABLE 10-continued effect of reaction temperature on the yield of (S)-nicotine

| No. | reaction temperature (° C.) | yield of (S)-nicotine (%) |
| --- | --- | --- |
| Example 29 | 10 | 45 |
| Example 30 | 5 | 48 |

Examples 31-32 differ from example 16 only in that the reaction temperature is varied in Step B4 reaction, as shown in Table 11.

TABLE 11 effect of reaction temperature on the yield of (S)-nicotine

| No. | reaction temperature (° C.) | yield of (S)-nicotine (%) |
| --- | --- | --- |
| Example 16 | 0 | 52 |
| Example 31 | 10 | 43 |
| Example 32 | −10 | 48 |

Examples 33-34 differ from example 16 only in that the use amount of oxalyl chloride is varied in Step B4 reaction, as shown in Table 12.

TABLE 12 effect of the use amount of oxalyl chloride on the yield of (S)-nicotine

| No. | eq. of oxalyl chloride (eq) | yield of (S)-nicotine (%) |
| --- | --- | --- |
| Example 16 | 1.5 | 52 |
| Example 33 | 1 | 48 |
| Example 34 | 2 | 35 |

A difference between Example 35 and Example 16 is that: in Step B1, the methyl nicotinate was replaced with equimolar ethyl nicotinate (with a CAS No. of 614-18-6), and produced (S)-nicotine had a yield of 52%, an ee value of 98%, and a purity of 99%.

The specific embodiments are merely an explanation of the present application and are not intended to limit the present application. After reading the present description, those skilled in the art can make modifications to the present embodiments as required without any inventive contribution, and these modifications shall fall within the scope of protection of the present application.

What is claimed is:

1. A synthesis method of chiral nicotine from nicotinate and γ-butyrolactone as raw materials, comprising the following steps:
    Step S1: performing condensation under an alkaline condition, and performing ring opening reaction with hydrochloric acid;
    Step S2: reacting with (+)—B-diisopinocampheyl chloroborane to produce a chiral hydroxyl group;
    Step S3: performing a chlorination reaction; and
    Step S4: performing cyclization under an alkaline condition to obtain the chiral nicotine.

2. The synthesis method of chiral nicotine according to claim 1, wherein an amination reaction is performed between Step S1 and Step S2, and an amine methylation reaction is performed following the cyclization in Step S4.

3. The synthesis method of chiral nicotine according to claim 1, comprising the following steps:
    Step A1: performing condensation reaction on nicotinate and Y-butyrolactone, and performing ring opening reaction with hydrochloric acid to obtain 4-chloro-1-(3-pyridinyl)-1-butanone;
    Step A2: reacting the 4-chloro-1-(3-pyridinyl)-1-butanone with (+)—B-diisopinocampheyl chloroborane to obtain (S)-4-chloro-1-(pyridin-3-yl)butan-1-ol;
    Step A3: reacting the (S)-4-chloro-1-(pyridin-3-yl)butan-1-ol with a chlorination reagent to obtain (S)-3-(1,4-dichlorobutyl) pyridine; and
    Step A4: performing cyclization reaction on the (S)-3-(1,4-dichlorobutyl) pyridine using an amination reagent under an alkaline condition to obtain S-demethylnicotine or (S)-nicotine; wherein the S-demethylnicotine is subjected to amine methylation to obtain (S)-nicotine.

4. The synthesis method of chiral nicotine according to claim 2, comprising the following steps:
    Step B1: adding nicotinate and γ-butyrolactone to organic solvent I and performing condensation at the present of an alkaline catalyst to obtain a condensation product, and subjecting the condensation product to ring opening at the presence of hydrochloric acid to obtain 4-chloro-1-(3-pyridine)-1-butanone;
    Step B2: reacting 4-chloro-1-(3-pyridine)-1-butanone with an amination reagent under an alkaline condition to obtain 4-amino-1-(3-pyridine)-1-butanone;
    Step B3: reacting 4-amino-1-(3-pyridine)-1-butanone with (+)—B-diisopinocampheyl chloroborane in an organic solvent H at -30-10° C. to obtain (S)-4-amino-1-(pyridin-3-yl) butan-1-ol;
    Step B4: reacting (S)-4-amino-1-(pyridin-3-yl) butan-1-ol with a chlorination reagent to obtain (S)-4-amino-1-(pyridin-3-yl) butyl-1-chloride; and
    Step B5: performing cyclization on (S)-4-amino-1-(pyridin-3-yl) butyl-1-chloride at the presence of a base to obtain (S)-demethylnicotine, and reacting (S)-demethylnicotine with an amine methylation reagent to obtain (S)-nicotine.

5. The synthesis method of chiral nicotine according to claim 3, wherein, in Step A4, the amination reagent is a methylamine salt amination reagent or an amino amination reagent.

6. The synthesis method of chiral nicotine according to claim 5, wherein, in Step A4, when the amination reagent is a methylamine salt amination reagent, (S)-3-(1,4-dichlorobutyl) pyridine is reacted with the amination reagent under an alkaline condition to obtain (S)-nicotine.

7. The synthesis method of chiral nicotine according to claim 6, wherein, in Step A4, when the amination reagent is a methylamine salt amination reagent, a molar ratio of (S)-3-(1,4-dichlorobutyl) pyridine to methylamine salt amination reagent is 1: (1-5).

8. The synthesis method of chiral nicotine according to claim 5, wherein, the methylamine salt amination reagent is any one selected from the group consisting of methylamine hydrochloride, methylamine sulfate and methylamine nitrate.

9. The synthesis method of chiral nicotine according to claim 5, wherein, when the amination reagent is an amino amination reagent, (S)-3-(1,4- dichlorobutyl) pyridine is reacted with the amination reagent under an alkaline condition to obtain (S)-demethylnicotine.

10. The synthesis method of chiral nicotine according to claim 9, wherein, a molar ratio of (S)-3-(1,4-dichlorobutyl) pyridine to amino amination reagent is 1: (3-8).

11. The synthesis method of chiral nicotine according to claim 9, wherein, the amino amination reagent is any one selected from the group consisting of formamide, tert-butyl carbamate and ammonium hydroxide.

12. The synthesis method of chiral nicotine according to claim 4, wherein, in Step B3, a molar ratio of the 4-amino-1-(3-pyridine)-1-butanone to (+)—B-diisopinocampheyl chloroborane is 1:(1-3).

13. The synthesis method of chiral nicotine according to claim 4, wherein, in Step B4, in Step B4, the chlorination reagent is oxalyl chloride, and a molar ratio of (S)-4-amino-1-(pyridin-3-yl) butan-1-ol to oxalyl chloride is 1:(1-3).

14. The synthesis method of chiral nicotine according to claim 4, wherein, in Step B2, the amination reagent is ammonia or formamide.

15. The synthesis method of chiral nicotine according to claim 4, wherein, in Step B2, a molar ratio of the 4-chloro-1-(3-pyridine)-1-butanone to the amination reagent is 1:(1-3).

16. The synthesis method of chiral nicotine according to claim 4, wherein, in Step B1, a mole ratio of nicotinate, γ-butyrolactone and the alkaline catalyst is 1: (1-2): (1.2-3).

17. A synthesis method of chiral nicotine from butyrolactone, comprising the following steps:
   Step C1: performing condensation reaction on nicotinate and γ-butyrolactone, and performing ring opening reaction with hydrochloric acid to obtain 4-chloro-1-(3-pyridinyl)-1-butanone;
   Step C2: reacting the 4-chloro-1-(3-pyridinyl)-1-butanone with (+)—B-diisopinocampheyl chloroborane to obtain (S)-4-chloro-1-(pyridin-3-yl)butan-1-ol;
   Step C3: reacting the (S)-4-chloro-1-(pyridin-3-yl)butan-1-ol with a chlorination reagent to obtain (S)-3-(1,4-dichlorobutyl) pyridine; and
   Step C4: performing cyclization reaction on the (S)-3-(1,4-dichlorobutyl) pyridine using an amination reagent under an alkaline condition to obtain S-demethylnicotine or (S)-nicotine; wherein the S-demethylnicotine is subjected to amine methylation to obtain (S)-nicotine.

18. The synthesis method of chiral nicotine according to claim 17, wherein, in Step C4, the amination reagent is a methylamine salt amination reagent or an amino amination reagent.

19. The synthesis method of chiral nicotine according to claim 18, wherein, when the amination reagent is a methylamine salt amination reagent, (S)-3-(1,4-dichlorobutyl) pyridine is reacted with the amination reagent under an alkaline condition to obtain (S)-nicotine.

20. The synthesis method of chiral nicotine according to claim 19, wherein, a molar ratio of (S)-3-(1,4-dichlorobutyl) pyridine to methylamine salt amination reagent is 1: (1-5).

* * * * *